United States Patent [19]
Fleming et al.

[11] Patent Number: 5,922,765
[45] Date of Patent: Jul. 13, 1999

[54] METHODS AND COMPOSITIONS FOR THE PREVENTION AND TREATMENT OF MUSCLE CRAMPS AND IMPROVING MUSCULAR STRENGTH

[75] Inventors: Thomas E. Fleming, St. Louis, Mo.; Herbert C. Mansmann, Jr., Newton Square, Pa.

[73] Assignee: Fleming & Company, Pharmaceuticals, Fenton, Mo.

[21] Appl. No.: 08/844,988

[22] Filed: Apr. 23, 1997

Related U.S. Application Data

[63] Continuation-in-part of application No. 08/588,564, Jan. 18, 1996.

[51] Int. Cl.$^6$ .................................................. A61K 31/19
[52] U.S. Cl. ............................................ 514/557; 514/558
[58] Field of Search ..................................... 514/557, 558

[56] References Cited

U.S. PATENT DOCUMENTS

| | | |
|---|---|---|
| 5,002,780 | 3/1991 | Bakta et al. . |
| 5,260,279 | 11/1993 | Greenberg . |
| 5,504,072 | 4/1996 | Schmidl et al. . |
| 5,550,166 | 8/1996 | Ostlund et al. . |

OTHER PUBLICATIONS

Kleefeld, Ann. Ocul., 1973.
Kleefeld, Bull. Soc. Belg. opht., 1973.
Mansmann, Jr., H.C., "Consider Magnesium Homeostasis" *Pediatric Asthma, Allergy& Immunology*, 5, pp. 273–279 (1991).
Physicians' Desk Reference, 50th Edition (1996) p. 1005, "Magonate Tablets, Magonate Liquid".
Bardicef, M., et al, 1995, *Am. J. Obstet. Gynecol.*, 172: 1009–1013.
Chen, Y–T, in *Internal Medicine*, ed. W.N. Kelley, 2270–2273 J.B. Lippincott (1972).
Davies, K.J.A., et al., 1982, *Biochem. Biophys. Res. Commun.*, 107:1198–1205.
Del Maestro, R.F., 1980, *Acta. Physiol. Scand.*, 492 (Suppl.): 153–168.
Deuster, P.A. et al., 1987, *Clin. Chem.*, 33: 529–532.
Deuster, P.A., et al., 1987, *J. Appl. Physiol.*, 62: 545–550.
Elin, R.J., 1987, *Clin. Chem.*, 33: 1965–1970.
Fantone, J.C., et. al., 1982, *Am. J. Pathol.*, 107: 395–418.
Fridovich, I., 1983, *Annu. Rev. Pharmacol. Toxicol.*, 23: 239–257.
Janssen, Y.M., et al., 1993, *Lab. Invest.*, 69: 261–274.
Mak, I.T. et. al., 1990, *Biochem. Pharm.*, 40: 2169–2175.
Mak, I.T., et al., 1995, *Biochem. Pharmacol.*, 50: 1531–1534.
Mak, I.T. & Weglicki, W.B., 1994, *Method Enzymol.*, 234: 620–630.
McDonald, R., et al., 1988, *Sports Med.*, 5: 171–184.
National Research Council, *Recommended Dietary Allowances*, 10th ed. Washington, D.C.: National Academy Press, 1989, pp. 1, 10–23, 174–205.
Ntoso, K.A and Goldfarb, S., in *Internal Medicine* ed. J.H. Stein, 2345–2349, Little, Brown and Company, Inc., (1990).
Pao, E.M., Micke, S.J., 1981, *Food Technol.*, 35: 58–69.
Rakel, R.E. ed. *Textbook of Family Practice*, 3rd ed, W.B. Saunders Co., (1984) 691–692.
Rose, L.I., et. al., 1970, *J. Appl. Physiol.*, 29: 449–451.
Tribble, D.L., et. al., 1987, *Hepatology*, 7: 377–386.
Rayssiquier, Magnesium Research (1990) 3,2, 93–102.

*Primary Examiner*—Rebecca Cook
*Attorney, Agent, or Firm*—Senniger, Powers, Leavitt & Roedel

[57] ABSTRACT

The present invention relates to methods and compositions for the prevention and/or treatment of exercise-induced muscle cramps, stiffness, pain or spasms, using magnesium gluconate alone or in combination with one or more antioxidants or conventional pharmacologic therapy. The invention also relates to inhibition of production of oxygenated molecules, oxygen free radicals and lipid peroxidation.

8 Claims, 4 Drawing Sheets

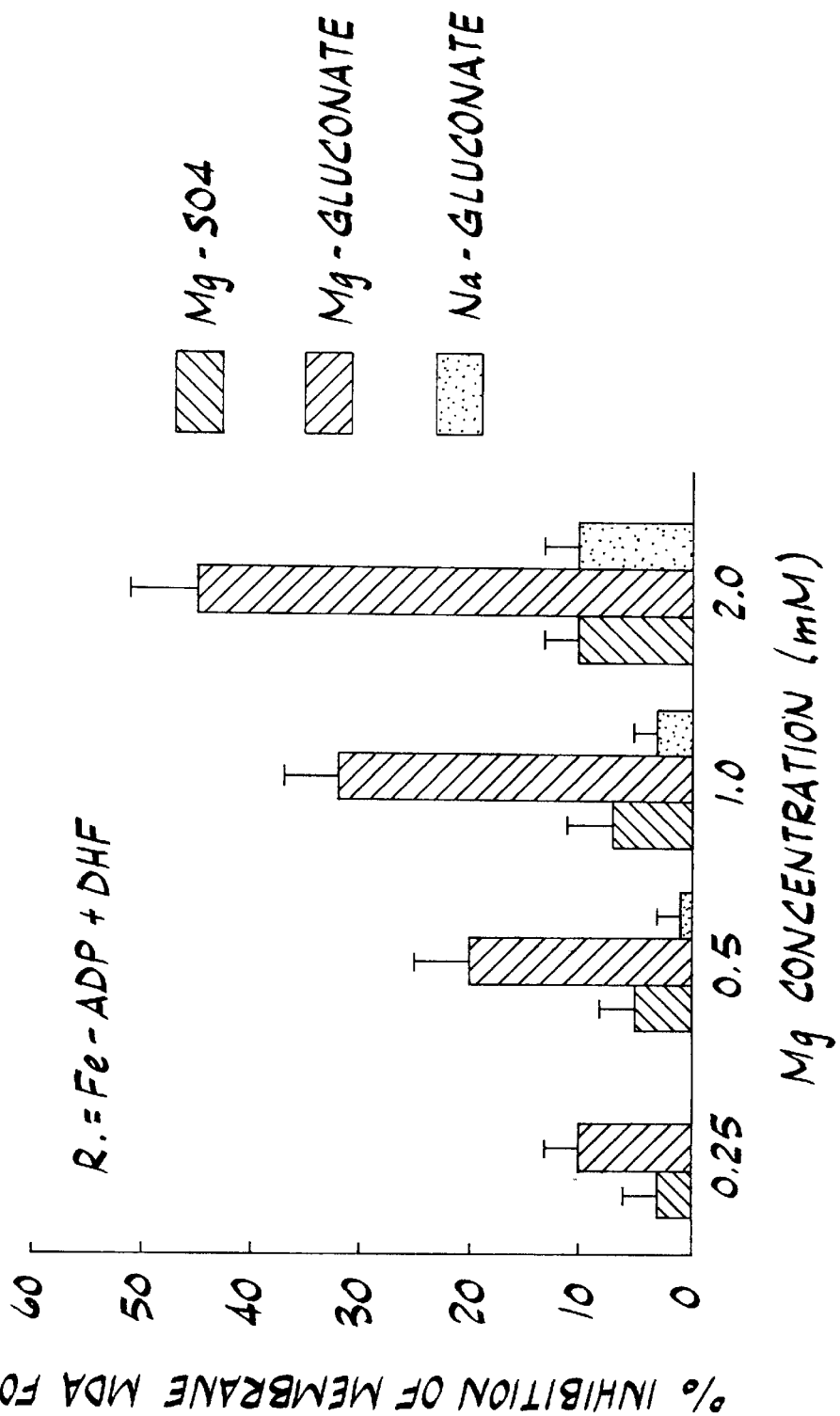

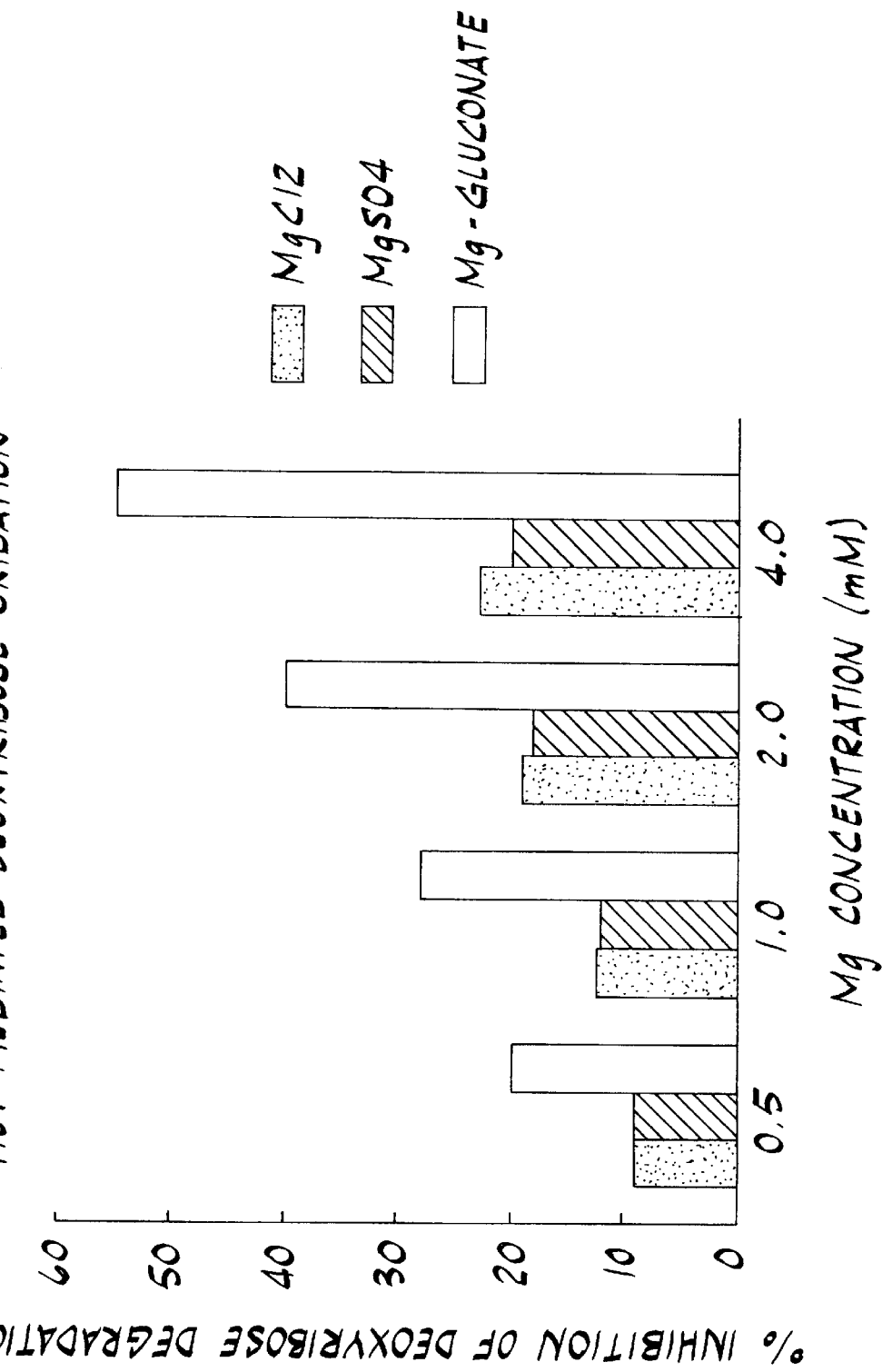

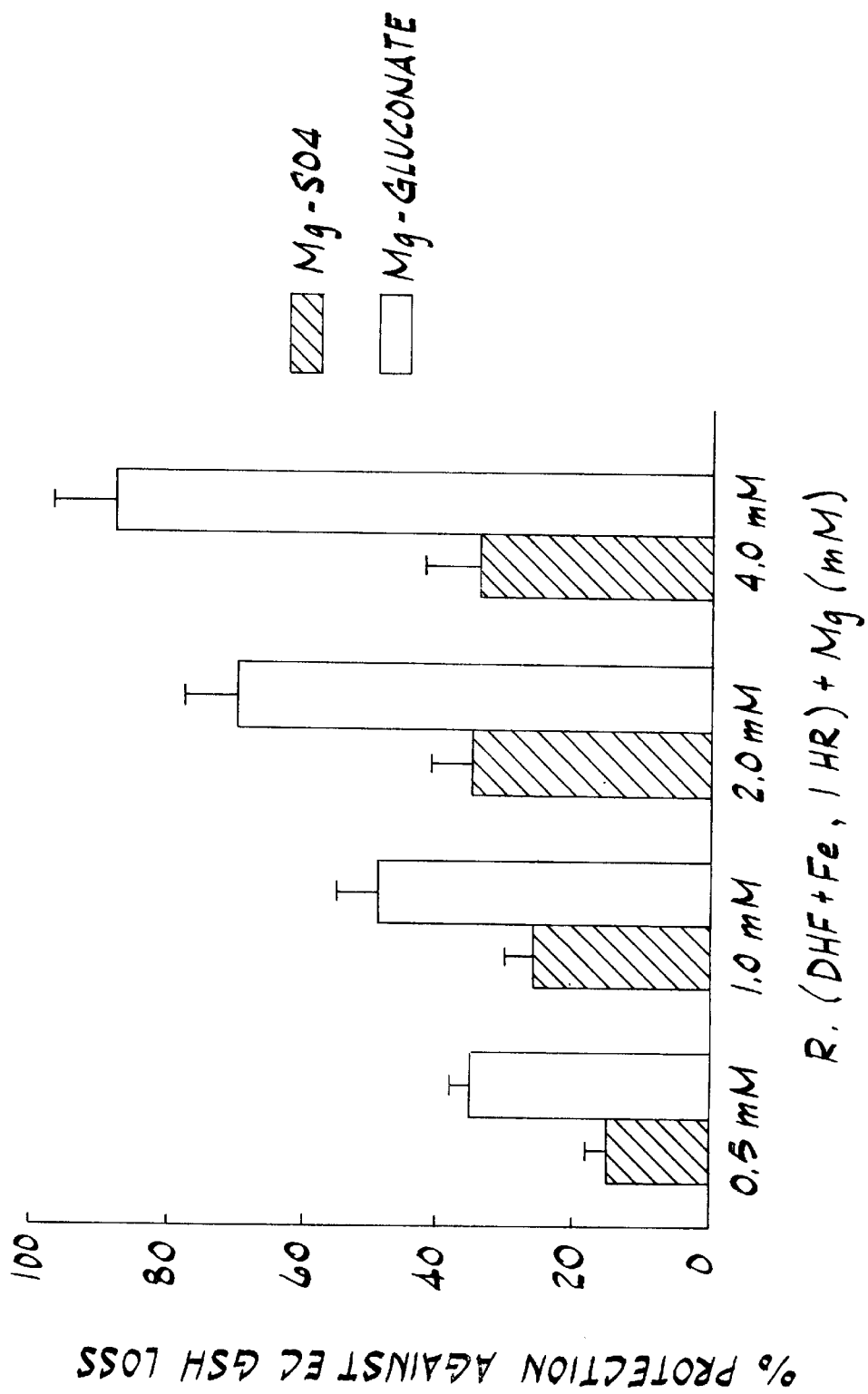

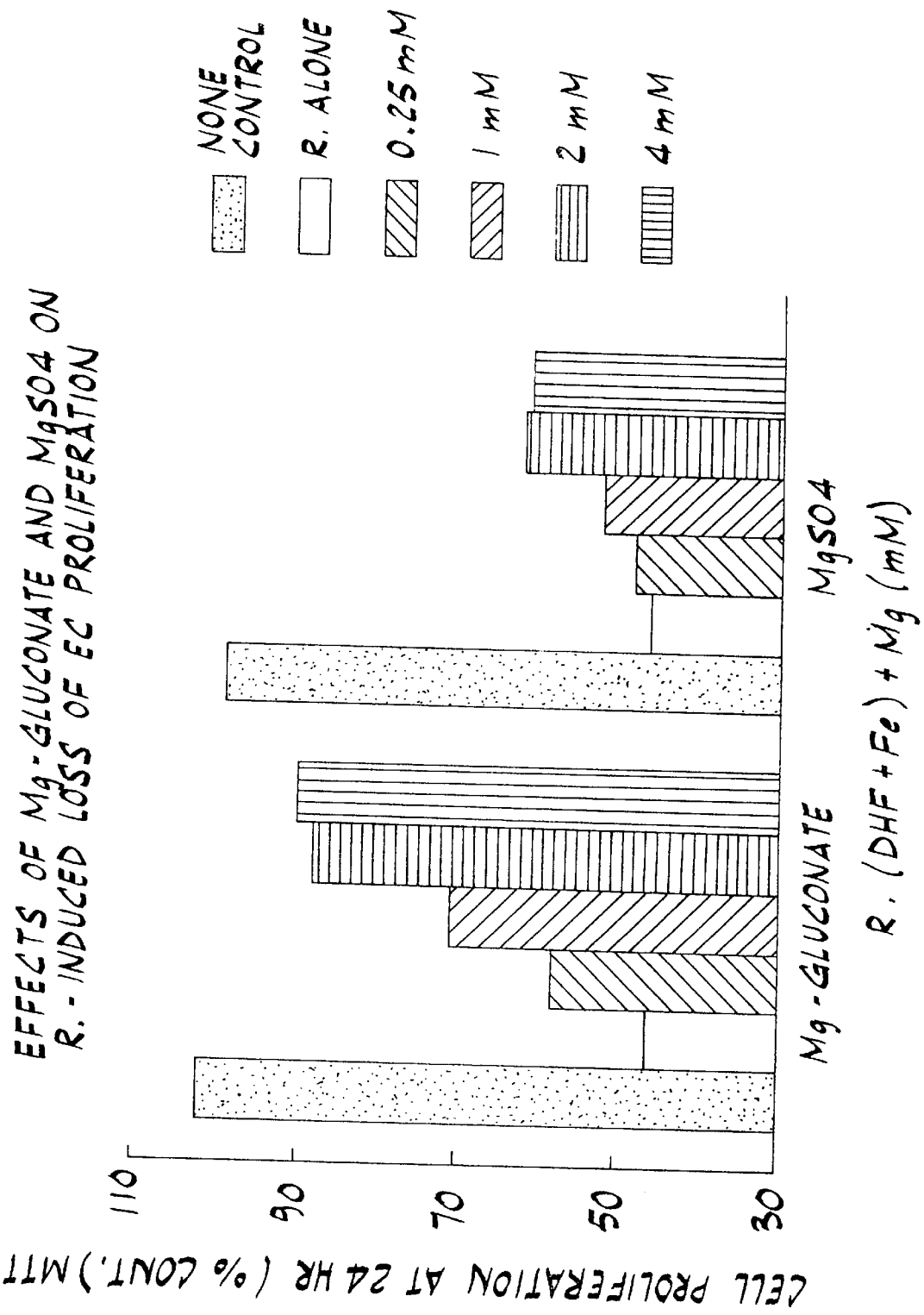

METHODS AND COMPOSITIONS FOR THE PREVENTION AND TREATMENT OF MUSCLE CRAMPS AND IMPROVING MUSCULAR STRENGTH

The present application is a Continuation-in-Part of application Ser. No. 08/588,564 filed Jan. 18, 1996, which is incorporated by reference herein in its entirety.

1. INTRODUCTION

The present invention relates to methods and compositions for the prevention and treatment of muscle cramps, stiffness, pain and spasms and for improving muscular strength. The methods and compositions of the invention are especially suitable for parenteral or enteral administration and are useful in preventing and/or treating neuromuscular problems and exercise-induced muscle cramps or free radicals in muscle.

2. BACKGROUND OF THE INVENTION

2.1 Exercise-Induced Muscle Trauma

Many sports put the participants at risk of direct trauma to muscle, tendon, ligament and subcutaneous tissues, e.g., by contact with the ground, the opponent, a ball or a bat. Much of the pain and disability resulting from soft-tissue trauma is due not to the injury itself but to bleeding in and around the damaged tissue. Extravasated blood causes pain by limiting movement and by local inflammation caused by pro-inflammatory mediators.

Magnesium homeostasis is essential to good health and proper neuromuscular function and magnesium deficiency may result in neuromuscular problems such as muscle cramps, stiffness, pain and spasms. For most athletes performing strenuous exercise, magnesium may be lost from the body. Sweating appears to account for some of this loss. McDonald, R., et. al., 1988, *Sports Med.,* 5: 171–184. However, most magnesium is lost via urinary excretion after exercise, which may be due to metabolic acidosis and increases in aldosterone and antidiuretic hormone. Rayssiguier, Y. et. al., 1990, *Magnesium Res.,* 3: 93–102.

2.2 Neuromuscular Effects

The neuromuscular effects of hypomagnesemia occur commonly in association with hypocalcemia and/or hypokalemia-although the symptoms and signs may be seen in the absence of any other electrolyte abnormalities. Hypomagnesemia associated neuromuscular abnormalities include Trousseau's or Chvostek's signs, tetany, muscle fasciculation, tremor, muscle spasticity, deep tendon reflexes, anxiety, delirium, grand mal seizures, nystagmus, ataxia, vertigo, choreoathetoid movements and dysphagia. Almost all conditions resolve quickly with magnesium replacement. Ntoso, K. A and Goldfarb, S., in *Internal Medicine* ed. J. H. Stein, 2345–2349, Little, Brown and Company, Inc., (1990). In adolescence, magnesium deficiency may also be associated with muscle pain, early fatigue and stiffness, growing pains and/or Osgood-Schlatter's disease or cramps on strenuous exertion in patients having muscle glycogeneses, Chen, Y-T, in *Internal Medicine,* ed. W. N. Kelley, 2270–2273 J. B. Lippincott (1992).

2.3 Magnesium

Magnesium is an important element for health and disease. It is the fourth most abundant cation in the human body and is the second most abundant intracellular cation. Elin, R. J., 1987, *Clin. Chem.,* 33: 1965–1970. Magnesium is a cofactor for approximately 300 enzymes and is essential for energy metabolism and for protein and nucleic acid synthesis. Magnesium deficiency may result from a number of factors including decreased intake or increased gastrointestinal or renal loss of magnesium, drug therapy, and alterations in magnesium distribution. Hypomagnesemia is generally defined as a serum magnesium concentration of less than 1.5 mEq/l. The signs and symptoms of hypomagnesemia include arrhythmias, electrocardiographic changes, hypertension, depression, delirium, agitation, tetany, leg cramps, tremors, ataxia, weakness, confusion and convulsions. The ideal intake of magnesium for an adult is 15 to 20 mM/d (350 to 450 mg/d). Magnesium is absorbed primarily in the jejunum and ileum, and healthy persons absorb about 30 to 40 percent of ingested magnesium. The majority of adults have a dietary intake of magnesium less than the recommended dietary allowance (RDA) in the range of 43 to 93.0 percent of RDA. Pao, E. M., Micke, S. J., 1981, *Food Technol.,* 35: 58–69.

Magnesium functions in a wide range of biochemical and physiological processes. Inside cells, magnesium serves as a modulator of many rate limiting enzymes. Extracellular levels of magnesium play an important role in muscle and nerve excitability by maintaining electrical potentials at the membrane. National Research Council, *Recommended Dietary Allowances,* 10th ed. Washington, D.C.: National Academy Press, 1989, pp. 1, 10–23, 174–205.

3. SUMMARY OF THE INVENTION

The present invention relates to methods and compositions for the prevention and treatment of muscle cramps, stiffness, pain and spasms, utilizing an effective amount of magnesium gluconate. The methods and compositions of the invention are especially useful in preventing and/or treating neuromuscular problems and exercise-induced muscle cramps or free radicals in muscle.

The present invention also relates to methods and compositions for improving muscle strength.

The present invention also contemplates the prevention and treatment of muscle cramps, stiffness, pain and spasms using an effective amount of magnesium gluconate along with conventional therapy for such conditions.

The present invention also provides a method for treating and/or preventing neuromuscular problems and damage caused by inflammatory reactions and/or oxygen free radicals, by providing a therapeutically effective amount of magnesium gluconate.

The present invention also provides a method for improving muscular strength in a human subject by using an effective amount of magnesium gluconate.

4. DESCRIPTION OF THE FIGURES

FIG. 1. Effects of magnesium salts on free radical mediated membrane lipid peroxidation.

FIG. 2. Effect of magnesium salts on site-specific OH.-mediated deoxyribose oxidation.

FIG. 3. Effect of magnesium salts on R.-induced loss of BA-endothelial cell glutathione.

FIG. 4. Effect of magnesium salts on R.-induced loss of endothelial cell proliferation.

5. DETAILED DESCRIPTION OF THE INVENTION

The present invention relates to methods and compositions for the prevention and treatment of muscle cramps, stiffness, pain and spasms. The present invention also provides a method for treating and/or preventing neuromuscular problems and exercise-induced muscle cramps or free radicals in muscles of athletes.

Neuromuscular problems or abnormalities associated with hypomagnesemia also include Trousseau's or Chvostek's signs, tetany, muscle fasciculation, tremor, muscle spasticity, deep tendon reflexes, anxiety, delirium, grand mal seizures, nystagmus, ataxia, vertigo, choreoathetoid movements or dysphagia. Other muscle conditions associated with magnesium deficiency especially in adolescence, include muscle pain, early fatigue and stiffness, growing pains and/or Osgood-Schlatter's disease or cramps on strenuous exertion.

The invention also provides a method for treating and/or preventing inflammatory reactions and inhibiting production of oxygen free radicals during strenuous exercise in athletes.

The present invention is also directed to a method for the prevention and treatment of muscle cramps, stiffness, pain and spasms using an effective amount of magnesium gluconate along with conventional therapy for such conditions.

The invention also provides a method for improving muscular strength in a human subject.

The present invention further relates to compositions containing magnesium gluconate in combination with antioxidants such as vitamin E, selenium, glutathione, glutathione isopropyl ester, or N-acetylcysteine, for use in the prevention and/or treatment of muscle cramps, stiffness, pain and spasms, and for improving muscular strength in a human subject.

"Conventional therapy" for muscle cramps and related conditions, as used herein includes muscle relaxants (e.g. diazepan) or antiinflammatory agents (e.g. ibuprofen).

"Oxygen free radical" as used herein refers to a free radical molecule with an odd, unpaired electron which makes the molecule unstable and highly reactive. Tribble, D. L., et. al., 1987, *Hepatology*, 7: 377–386. Small amounts of these free radicals are produced endogenously by the mitochondrial electron transport system and the endoplasmic reticulum in microsomes and peroxisomes. Oxygen free radicals, the superoxide anion ($O_2^-$) the hydroxyl radical ($°OH$), and their intermediary, hydrogen peroxide ($H_2O_2$) are believed to be generated in vascular complications associated with exercise-induced muscle cramps, stiffness, pain or spasms, e.g., platelet aggregation, vasoconstriction and bronchoconstriction. The free radicals interact with other cellular constituents such as deoxyribonucleic acid (DNA) and lipids and lead to subsequent formation of multiple degradation products. Lipid peroxidation forms lipid peroxides and aldehydes that interact with protein sulfhydryl groups and thereby perpetuate cellular damage. Del Maestro, R. F., 1980, *Acta. Physiol. Scand.*, 492 (Suppl.): 153–168.

Normally, protective mechanisms are present in the cell to prevent damage by free radicals. For example, the primary mechanism of clearance of $O_2^-$ from biologic systems is superoxide dismutase, which catalyses the dismutation of $O_2^-$ to $H_2O_2$ and $O_2$. The cytoplasmic enzymes glutathione peroxidase and catalase provide the final detoxification steps with the reduction of $H_2O_2$ to $O_2^-$ Glutathione peroxidase seems to be a more active enzyme than catalase in protecting cells such as myocardial cells or endothelial cells from $H_2O_2$-mediated damage. Fridovich, I., 1983, *Annu. Rev. Pharmacol. Toxicol.*, 23: 239–257; Fantone, J. C., et. al., 1982, *Am. J. Pathol.*, 107: 395–418.

The present invention provides a method comprising administering to a human subject at risk of exercise-induced muscle cramps, stiffness, pain or spasms, a composition comprising magnesium gluconate in sufficient amounts to inhibit oxygen free radical production and lipid peroxidation.

In different embodiments of the invention, the composition of the invention may be administered enterally or parenterally in the prevention or treatment of muscle cramps, stiffness, pain or spasms and in improving muscle strength.

The compositions of the invention may comprise tablets, capsules, powder preparations, aqueous solutions and nutrient preparations containing magnesium gluconate in an amount sufficient to inhibit oxygen free radical production and lipid peroxidation in various vascular and membrane tissues.

Administration of magnesium gluconate results in cellular resistance to oxygen free radical stress and free radical production, for example lipid peroxides.

Magnesium is an important metallo coenzyme for many enzyme reactions. In the method of the present invention, magnesium gluconate inhibits the production of free radicals, reduces cellular damage due to oxidative stress, reduces lipid peroxidation and reduces glutathione loss.

Spontaneous or exercise-related discomfort from muscles is usually benign and does not signal chronic disease. The terms cramp, pain and spasm are often used interchangeably to describe symptoms referred to muscles. Other terms, such as aching and stiffness are also used.

"Cramp" as used herein, refers to a spontaneous, prolonged and painful contraction of one or more muscles. Muscle pain may be associated with strenuous exercise or fatigue. Cramping or muscle spasm is a common complaint in athletes and has multiple causes. There is a distinction between the cramp that occurs with effort or injury and the cramp that occurs at rest at night (nocturnal cramp). Cramps in athletes may occur during exercise when a relative arterial insufficiency in blood flow arises or when transient ischemia caused by isometric contractions in overused muscle groups occurs. Injury to the muscle, by a blow that causes slight infiltration of blood, overstretching of a muscle with resultant tearing of some fibers, or strain by overcontraction of the muscle against resistance frequently leads to muscle cramps or spasm. Some cramps may appear without warning and without any apparent etiology. In a hot climate overheating, or excessive sweating leading to a decrease in body electrolyte content, may cause muscle spasm. Sudden chilling may cause cramping or spasm. A build-up of carbondioxide or lactic acid in the muscle and a decrease in oxygenation may also cause cramping. R. E. Rakel, ed. Textbook of Family Practice, 3rd ed, W.B. Saunders Co., 691–692 (1984).

"Spasm" as used herein, refers to a brief, unsustained abnormal contraction of a single or multiple muscles. Abnormal movements of muscle may arise from abnormal electrical activity of the central nervous system mediated via the motor neuron or muscle fiber itself.

5.1 Effects of Exercise on Magnesium Status and Muscular Strength

Although magnesium status may not appear to be compromised, there are several reports showing that magnesium may be lost from the body after performing strenuous exercise and the reduced levels may be undetectable by blood chemistry. Blood levels of magnesium are altered by exercise. For example, serum levels of magnesium were found to be significantly lower than baseline after thirty minutes of swimming (Laires, M. J., et. al., 1991, *Magnes.*

Res., 4: 119–122), after a 120-km hike (Stendig-Lindberg, G. Y., et. al., 1988, Am. J. Coll. Nutr., 6: 35–40), after a marathon race in eight runners (Rose, L. I., et. al., 1970, J. Appl. Physiol., 29: 449–451), and after high-intensity anaerobic treadmill running in thirteen men (Deuster, P. A., et. al., 1987, J. Appl. Physiol., 62: 545–550). However, these losses appear to be made up by the diet after extended periods of time (Stendig-Lindberg, G. Y., et. al., 1988, Am. J. Coll. Nutr., 6: 35–40), because most athletes do not show a compromised magnesium status.

Magnesium homeostasis is essential to good health and proper neuromuscular function and magnesium deficiency may result in neuromuscular problems such as muscle cramps, stiffness, pain and spasms.

The rate of cellular respiration increases during exercise in order to facilitate oxygen delivery to the working muscle. In cellular respiration, during reduction of the molecular oxygen to water, partially reduced oxygen species are produced that are very reactive with protein, lipids, and DNA, producing deleterious effects and damage on cells by peroxidation of lipids. Janssen, Y. M., et. al., 1993, Lab. Invest., 69: 261–274. Since the reduction of molecular oxygen to water in the electron transport chain increases in contracting muscle, more oxygen free radicals are formed during exercise. Thus, exercise induced free radicals may cause damage to mitochondrial membranes in a chronic training situation. Davies, K. J. A., et. al., 1982, Biochem. Biophys. Res. Commun., 107: 1198–1205.

The exact nature of the relationship between magnesium and muscle strength or exercise-induced muscle cramps, stiffness, pain or spasms remains to be explained. However, the compositions and methods of the present invention are especially suited for use in improving muscle strength and in the treatment and prevention of exercise-induced muscle cramps, stiffness, pain or spasms by virtue of their enhanced properties as antioxidants compared with other magnesium salts as described infra, in Section 6, and by virtue of having minimal purgative action on the gut.

5.2. Pharmaceutical Preparations and Methods of Administration

Magnesium gluconate compositions for use in accordance with the present invention are formulated by mixing magnesium gluconate into an aqueous solution or by mixing a suitable magnesium salt, for example, magnesium carbonate, with glucono-delta-lactone or magnesium carbonate with glucono-delta-lactone and/or citric acid. Desirably, the following concentrations are utilized: magnesium carbonate in the range of 2 mg per liter to 44 g per liter; citric acid in the range of 2.3 mg. per liter to 46.2 g per liter; and glucono-delta-lactone in the range of 6 mg per liter to 26 mg per liter. There results an aqueous solution of magnesium gluconate or magnesium gluconate/citrate, i.e., a solution containing magnesium gluconate and magnesium citrate that exerts unexpected and stronger antioxidant, antiperoxidative and cytoprotective effects than other magnesium salts, as described more fully in Section 7.0 below. In addition, magnesium gluconate may be included in a nutritional formula or in the form of tablets, capsules and powdered or granular preparations which are reconstituted to provide an aqueous composition.

Aqueous magnesium gluconate compositions of the invention comprise formulations suitable for enteral, parenteral and rectal administration.

The compositions of the present invention for preventing and/or treating exercise-induced muscle cramps, stiffness, pain or spasms, should be administered to a patient at therapeutically effective doses. A therapeutically effective dose refers to that amount of the magnesium compound sufficient to result in the amelioration of symptoms of exercise-induced muscle cramps, stiffness, pain or spasms. Similarly, a therapeutically effective dose refers to that amount of the antioxidants, including but not limited to, Vitamin E, selenium, glutathione, glutathione isopropyl ester or N-acetylcysteine, sufficient to result in the amelioration of symptoms of exercise-induced muscle cramps, stiffness, pain or spasms.

Toxicity and therapeutic efficacy of the magnesium compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% in the population). The dose ratio between toxic and therapeutic effects is the therapeutic index and it can be expressed as the ratio $LD_{50}/ED_{50}$. Compounds which exhibit large therapeutic indices are preferred. The data obtained from the cell culture assays and animal studies can be used in formulating a range of dosages for use in humans.

5.3 Formulations

Magnesium gluconate compositions for use in accordance with the present invention are formulated by mixing magnesium gluconate into an aqueous solution or by mixing a suitable magnesium salt, for example, magnesium carbonate, with glucono-delta-lactone or magnesium carbonate with glucono-delta-lactone and/or citric acid. Pharmaceutical compositions for use in accordance with the present invention can be formulated by conventional means in aqueous form, powdered preparations or by using one or more physiologically acceptable carriers, excipients or buffers.

Thus, the compounds and their physiologically acceptable salts and solvates can be formulated for administration by insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate or talc); disintegrants (e.g., potato starch or sodium starch glycolate); or wetting agents (e.g., sodium lauryl sulphate). The tablets can be coated by methods well known in the art. Liquid preparations for oral administration can take the form of, for example, aqueous solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydrobenzoates or sorbic acid). The preparations can also contain buffer salts, flavoring, coloring and sweetening agents as appropriate. The preparations can also take the form of powdered preparations or nutritional formulas.

Preparations for oral administration can be formulated to give controlled release of the active compound.

For buccal administration the compositions can take the form of tablets or lozenges formulated in the conventional manner.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, other glycerides or carbowaxes.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

Patient dosages for enteral or parenteral administration range from 10 to 150 mEq of magnesium gluconate per day, commonly 20–50 mEq per day, and typically from 20 to 30 mEq per day. Stated in terms of milligrams of Mg, dosages range from 100 mg per day to 1800 mg per day, commonly 250 mg to 600 mg per day.

Dosage amounts of antioxidants for enteral administration range from for example, for vitamin E: 200 to 1000 I.U. per day. Dosage amount and interval may be adjusted to provide plasma levels which are sufficient to maintain normal metabolism.

6. EXAMPLE

The antioxidant properties of magnesium gluconate were studied by incubating microsomal membranes prepared from endothelial cells in the presence of 0.25, 0.5, 1.0 and 2.0 mM of magnesium salts including magnesium gluconate, magnesium sulfate and magnesium chloride or sodium gluconate. Membrane malondialdehyde and site specific OH-mediated deoxyribose oxidation were measured according to methods described by Mak, I. T. & Weglicki, W. B., 1994, *Method Enzymol.*, 234: 620–630; and Mak, I. T. et. al., 1990, *Biochem. Pharm.*, 40: 2169–2175. Results demonstrate that magnesium gluconate is more effective than magnesium sulfate or sodium gluconate in inhibiting free radical production (e.g., malondialdehyde which also indicates $TXA_2$ production) (FIG. 1). Magnesium gluconate is also more effective than magnesium chloride or magnesium sulfate in inhibiting free radical mediated deoxyribose oxidation in a dose-related manner. (FIG. 2). These data indicate magnesium gluconate has unexpected and more powerful antioxidant properties and thromboxane inhibiting activity than other magnesium salts.

Cultured bovine aortic (BA) endothelial cells were incubated with R. (R.=0.83 mM dihydroxyfumarate+0.025 mM $Fe^{3+}$-ADP) for 50 mins at 37° C. Glutathione (GSH) was then determined by the enzymatic method described by Mak, I. T., et. al., 1992, *Cir. Res.*, 70: 1099–1103. A loss of 56% of total GSH was observed. When the cells were pretreated for 10 mins with varying amounts of magnesium gluconate or magnesium sulfate before being exposed to R., magnesium gluconate significantly prevented the GSH loss to varying degrees (p<0.05). The EC50 was 1.1 mM (FIG. 3).

When endothelial monolayers (about 65% confluent) were incubated with R. for 30 min, the cell survival/proliferation determined by the tetrazolium salt MTT assay (Mak, I. T., et. al., 1995, *Biochem. Pharmacol.*, 50: 1531–1534), decreased to 38% of control at 24 hr. Pretreatment with magnesium gluconate attenuated the loss in cell survival/proliferation (expressed as % of control (cont.)) in a dose-dependent manner compared with the cells pretreated with magnesium sulfate (FIG. 4).

It is important to note that the effects of magnesium sulfate on R.-induced loss of GSH or R.-induced losses of cell survival/proliferation were much lower than those obtained with magnesium gluconate, i.e., magnesium sulfate was approximately 33% as potent as magnesium gluconate (FIGS. 1–4).

7. EXAMPLE

Use of Magnesium Gluconate in Exercise-induced Muscle Cramps

The invention is illustrated, by way of protocols for exercise-induced muscle cramping in men over 35 years of age who experience muscle cramps, stiffness and pain during rugby playing.

The efficacy of oral magnesium gluconate (Magonate®-Fleming and Co., Pharmaceuticals) is compared with a matching placebo, sodium gluconate. 30 mL magnesium (324 mg Mg) is given before the start of a rugby game in 25 subjects. The magnesium status of each subject in the study is evaluated by measuring serum magnesium, erythrocyte magnesium concentrations, leukocyte magnesium concentration or 24-hour magnesium excretion before the start of the rugby game and after the game. Thus, there is a pre-game magnesium status measured for each subject. Each subject is used to test the effect of the placebo at the following rugby game. The methods employed to measure magnesium include use of ion-selective electrodes and nuclear magnetic resonance spectroscopy, as described by Elin, R. J., 1987, *Clin. Chem.*, 33: 1965–1970; and Deuster, P. A. et. al., 1987, *Clin. Chem.*, 33: 529–532; and Bardicef, M., et. al., 1995, *Am. J. Obstet. Gynecol.*, 172: 1009–1013.

Each subject is interviewed immediately post-game and the following information is recorded: cramping information (number, intensity, location, duration, amount of time cramping caused the subject to stop playing) and muscle pain or stiffness (frequency, intensity, location and duration).

The number of occurrences of cramps, pain or stiffness are reduced when the subjects receive magnesium gluconate before the start of the game as compared with when they receive sodium gluconate. Thus, the magnesium gluconate compositions of the present invention are useful in the prevention and/or treatment of muscle cramping, pain or stiffness.

The present invention is not to be construed as limited in scope to the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for preventing or treating exercise-induced muscle cramps, stiffness, pain or spasms caused by or related to production of oxygen free radicals in a human subject, the method comprising administering to the human subject an effective amount of magnesium gluconate.

2. The method of claim 1, wherein the magnesium gluconate is at a concentration range of approximately 0.1 mM to 1.5 M.

3. The method of claim 1, wherein the magnesium gluconate is administered enterally.

4. The method of claim 1, wherein the magnesium gluconate is administered parenterally.

5. The method of claim 1, wherein the magnesium gluconate is administered rectally.

6. The method of claim 1 further comprising administering a pharmaceutical agent selected from the group consisting of a muscle relaxant or an antiinflammatory agent.

7. The method of claim 1 further comprising administering one or more antioxidants selected from the group consisting of vitamin E, selenium, glutathione, glutathione isopropyl ester and N-acetylcysteine.

8. The method of claim 6 further comprising administering one or more antioxidants selected from the group consisting of vitamin E, selenium, glutathione, glutathione isopropyl ester and N-acetylcysteine.

* * * * *